United States Patent [19]

Hunter et al.

[11] 3,954,438

[45] May 4, 1976

[54] 5-TRIFLUOROMETHYL-7-AMINOBENZIMIDAZOLES HERBICIDES

[75] Inventors: Don L. Hunter; Robert A. Smith, both of Anaheim; Wayne S. Belles, Orange, all of Calif.

[73] Assignee: United States Borax & Chemical Corporation, Los Angeles, Calif.

[22] Filed: June 3, 1974

[21] Appl. No.: 476,012

Related U.S. Application Data

[63] Continuation-in-part of Ser. No. 333,902, Feb. 20, 1973, abandoned.

[52] U.S. Cl. .................................................. 71/92
[51] Int. Cl.² .......................................... A01N 9/22
[58] Field of Search ...................................... 71/92

[56] References Cited
UNITED STATES PATENTS

| | | |
|---|---|---|
| 3,325,271 | 6/1967 | Goldsmith et al. ............... 71/92 |
| 3,399,987 | 9/1968 | Woods et al. ..................... 71/92 |
| 3,472,865 | 10/1969 | Newbold et al. ............... 71/92 X |
| 3,472,866 | 10/1969 | Newbold et al. ............... 71/92 X |
| 3,531,495 | 9/1970 | Burton et al. ................. 71/92 X |
| 3,681,376 | 8/1972 | Scherer et al. ................ 71/92 X |
| 3,721,678 | 3/1973 | Burton et al. ................. 71/92 X |

*Primary Examiner*—Lewis Gotts
*Assistant Examiner*—Catherine L. Mills
*Attorney, Agent, or Firm*—James R. Thornton

[57] ABSTRACT

Benzimidazoles having 5-trifluoromethyl and 7-amino substituents are useful as herbicides. The 1-and 2-positions of the molecule also have at least one substituent; and, preferably both positions are substituted, such as with alkyl groups.

16 Claims, No Drawings

5-TRIFLUOROMETHYL-7-AMINOBENZIMIDAZOLES HERBICIDES

This is a continuation-in-part of our copending application Ser. No. 333,902 filed Feb. 20, 1973, now abandoned.

This invention relates to a novel class of substituted benzimidazoles and, more particularly, to a class of 5-trifluoromethyl-7-aminobenzimidazoles having utility as herbicides. The novel benzimidazoles of this invention have the formula

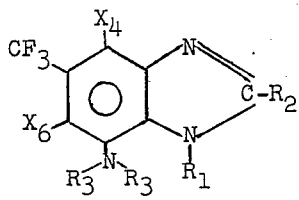

in which $R_1$ represents hydrogen, lower alkyl, halo-substituted lower alkyl, lower cycloalkyl, halo-substituted lower cycloalkyl, hydroxyl-substituted lower alkyl, lower alkoxy-substituted lower alkyl, or di-lower akylamino; $R_2$ represents hydrogen, lower alkyl, lower cycloalkyl, hydroxy-substituted lower alkyl, lower alkoxy-substituted lower alkyl, halo, or di-lower alkylamino; each $R_3$ is selected from the group consisting of hydrogen and lower alkyl; and each of $X_4$ and $X_6$ represents hydrogen, halo, lower alkoxy, or amino of the formula

Further, not more than one of $R_1$ and $R_2$ represents hydrogen and not more than one of $X_4$ and $X_6$ represents

Thus, the benzimidazoles have at least one amino group at the 7-position which may be unsubstituted or which may have one or two lower alkyl substituents. The present compounds must also have a trifluoromethyl group at the 5-position of the benzimidazole molecule. Other possible substituents include the halogens such as bromo, chloro, iodo and fluoro; lower alkoxy of 1 to about 6 carbon atoms such as methoxy, ethoxy, n-butoxy and n-hexyloxy; and an additional amino group which may be unsubstituted or which may have one or two lower alkyl substituents as defined by $R_3$.

$R_1$ and $R_2$ can each represent a lower alkyl or lower cycloalkyl substituent which may contain from 1 to about 6 carbon atoms and, optionally, may have one or more halo, hydroxy or lower alkoxy substituents. Examples of such groups include methyl, ethyl, n-propyl, isopropyl, sec-butyl, 3-pentyl, cyclopropyl, cyclobutyl, cyclohexyl, n-hexyl, 2-bromoethyl, 3-chloropropyl, 2-hydroxyethyl, 2-chlorocyclohexyl, 3-hydroxypropyl, chloromethyl, methoxymethyl, 3-ethoxypropyl, 2,2-dichloroethyl, 2-methoxyethyl, 1-methyl-2-methoxyethyl, 2,2-difluoroethyl, 2,2-diethoxyethyl, 4-hydroxybutyl, and the like. In a preferred embodiment, the hydrocarbon substituents represented by $R_1 + R_2$ contain a total of 2 to about 6 carbon atoms. Alternatively, $R_1$ and $R_2$ may represent a di-lower alkylamino group and $R_2$ can represent a halo group, especially bromo or chloro, as defined above.

The 1- or 2-positions of the benzimidazole molecule may be unsubstituted; however, at least one, and preferably both, of the 1- and 2-positions are substituted. Examples of compounds embraced by the formula above include those in which $X_4$ is hydrogen and $X_6$ is — chloro, and those in which both $R_3$'s in the 7-amino group are hydrogen. The compounds may also be in the salt form such as the hydrochloride. Representative compounds, according to the present invention include:

7-amino-2-ethyl-5-trifluoromethylbenzimidazole
7-amino-2-methyl-6-chloro-5-trifluoromethylbenzimidazole
7-amino-2-isopropyl-6-methoxy-5-trifluoromethylbenzimidazole
7-ethylamino-1-ethyl-2-methyl-5-trifluoromethylbenzimidazole
7-amino-1-ethyl-2-methyl-6-fluoro-5-trifluoromethylbenzimidazole
6,7-diamino-1-sec-butyl-2-ethyl-5-trifluoromethylbenzimidazole
7-dimethylamino-2-isopropyl-6-bromo-5-trifluoromethylbenzimidazole
7-amino-2-n-hexyl-5-trifluoromethylbenzimidazole
7-amino-4-chloro-2-ethyl-5-trifluoromethylbenzimidazole
7-methylamino-1-methyl-2-sec-butyl-6-ethoxy-5-trifluoromethylbenzimidazole
7-amino-2-chloro-5-trifluoromethylbenzimidazole
7-amino-2-(dimethylamino)-1-isopropyl-6-chloro-5-trifluoromethylbenzimidazole
7-amino-1-ethyl-2-(2-hydroxyethyl)-6-methoxy-5-trifluoromethylbenzimidazole
7-amino-1-isopropyl-2-bromo-6-methoxy-5-trifluoromethylbenzimidazole
7-amino-1-(1-methyl-2-methoxyethyl)-2-ethyl-5-trifluoromethylbenzimidazole
7-amino-1-ethyl-6-methoxy-2-methyl-5-trifluoromethylbenzimidazole
7-amino-1-ethyl-6-chloro-2-methyl-5-trifluoromethylbenzimidazole
7-amino-6-dimethylamino-1-ethyl-2-methyl-5-trifluoromethylbenzimidazole
7-amino-6-chloro-1-cyclopropyl-2-methyl-5-trifluoromethylbenzimidazole
7-amino-1-ethyl-2-methyl-5-trifluoromethylbenzimidazole
4,7-diamino-6-chloro-1-ethyl-2-isopropyl-5-trifluoromethylbenzimidazole
7-amino-4,6-dichloro-1-ethyl-2-methyl-5-trifluoromethylbenzimidazole
7-amino-6-chloro-1-isopropyl-5-trifluoromethylbenzimidazole
7-amino-1-ethyl-2-(methoxymethyl)-6-bromo-5-trifluoromethylbenzimidazole
7-amino-1-methyl-2-(diethylamino)-6-chloro-5-trifluoromethylbenzimidazole The compounds of this invention are generally crystalline solids, being soluble in organic solvents such as alcohol, acetone, the chlorinated hydrocarbons, benzene, etc. They are readily prepared by procedures known for the preparation of benzimidazoles such as the reaction of the corresponding substituted o-phenylenediamine with a carboxylic acid in the presence of a mineral acid according to the following equation

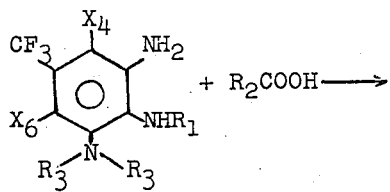

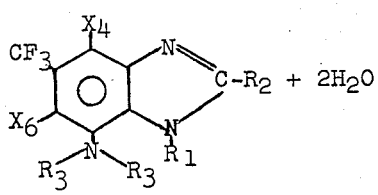

in which $R_1$, $R_2$, and $R_3$, $X_4$ and $X_6$ have the significance previously assigned.

Alternatively, a carboximidate or phosgeneimmonium chloride may be employed in place of the carboxylic acid. Such carboximidates have the formula

in which R' is lower alkyl such as ethyl, and are generally used in their hydrochloride form. A suitable synthesis is illustrated as follows:

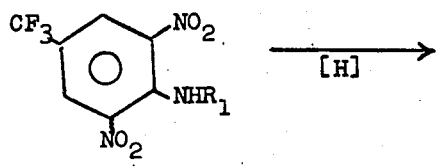

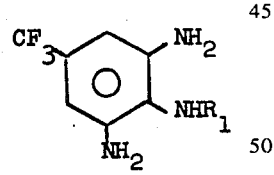

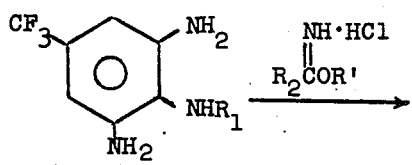

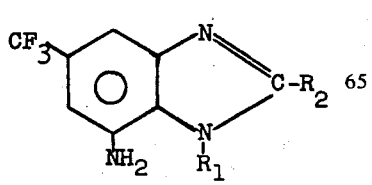

The phosgeneimmonium salt has the formula

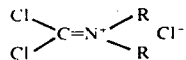

in which R is lower alkyl and a suitable synthesis is illustrated by the equation:

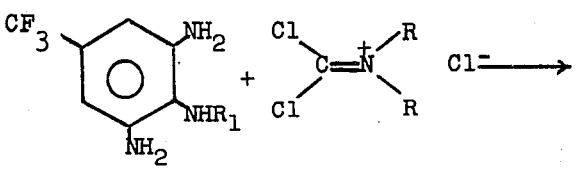

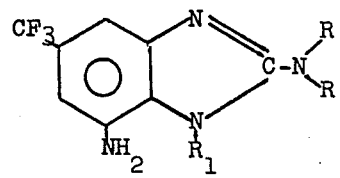

In many cases, such as when the 6-position is substituted it may be more convenient to prepare the 7-nitrobenzimidazole and then reduce the nitro group to an amino group such as with hydrogen in the presence of a catalyst such as platinum oxide. The nitro group may be present on the ortho-phenylenediamine prior to its conversion to the benzimidazole or, alternatively, a benzimidazole free of a 7-substituent may be nitrated, such as with nitric acid, to give the 7-nitro derivative, which is then reduced to the desired 7-amino derivative. A suitable synthesis is illutrated as follows.

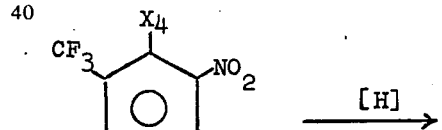

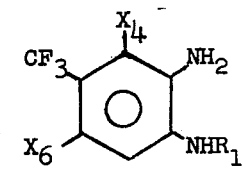

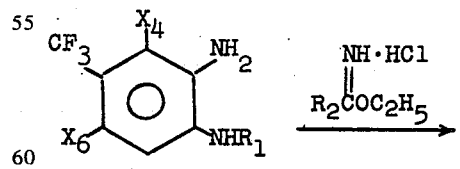

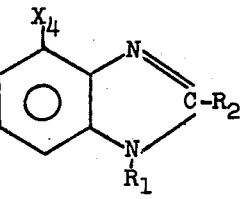

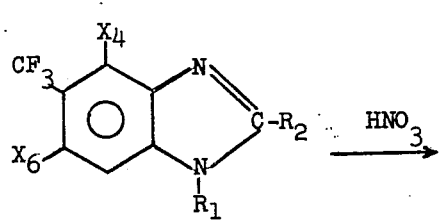
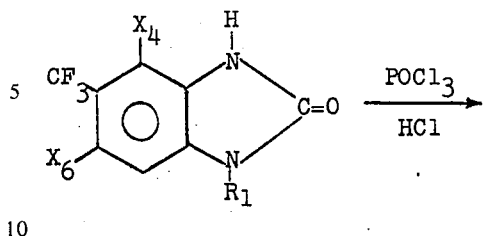

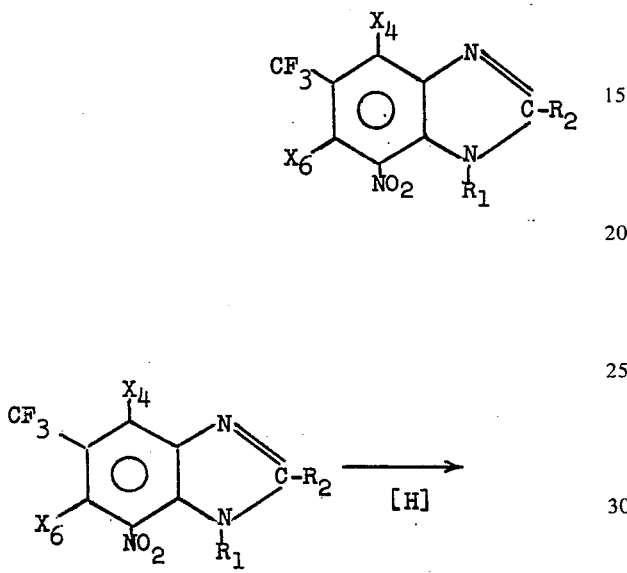

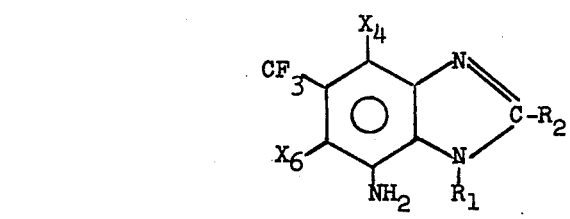

When $R_2$ is a halo group, the 7-nitrobenzimidazole compound can be prepared by halogenation of the corresponding benzimidazolone such as with phosphorus oxychloride or phosphorus oxybromide, such as illustrated below, and then nitration of the resultant 2-halobenzimidazole.

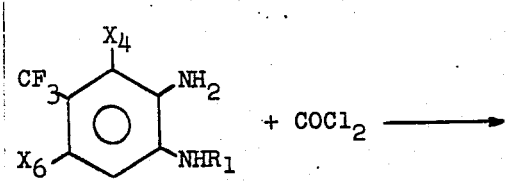

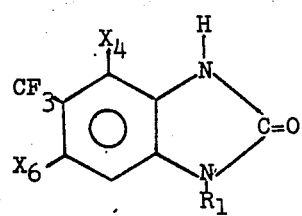

See British Pat. No. 1,298,020 which describes preparation of 2,6-dinitro-3-halo-4-trifluoromethylanilines by reaction of a 2,4-dihalo-3,5-dinitrobenzotrifluoride with an amine. The halo group can be replaced by an alkoxy or amino group by known procedures, if desired. See also U.S. Pat. No. 3,466,329 which shows the chemical reduction of 2,6-dinitro-4-trifluoromethylanilines employing sodium sulfide to produce the corresponding 6-nitro-4-trifluoromethyl-1,2-phenylenediamine.

The following examples illustrate the preparation of representative compounds of this invention and intermediates therefor.

EXAMPLE I

N-Ethyl-3-chloro-6-nitro-4-trifluoromethylaniline

Aqueous ethylamine (70%; 29.72g.; 0.46 mole) was added to a stirred solution of 60g. (0.23 mole) of 2,4-dichloro-5-nitrobenzotrifluoride in 200 ml. of dimethoxyethane. The mixture was stirred for two hours while the exotherm subsided and then heated near reflux temperature overnight. The resulting mixture was evaporated to dryness at reduced pressure and the residue dissolved in chloroform. After washing twice with water, the cholorform solution was dried over sodium sulfate, filtered, and the solvent removed from the filtrate by distillation under reduced pressure. Crystallization of the residue from 95% ethanol gave 57.0g. (87.1%) of N-ethyl-3-chloro-6-nitro-4-trifluoromethylaniline, m.p. 92.5°–94°C.

EXAMPLE II

6-Chloro-1-ethyl-2-methyl-5-trifluoromethylbenzimidazole

A hydrogenation bottle was charged with 28.9g. (0.1075 mole) of N-ethyl-3-chloro-6-nitro-4-trifluoromethylaniline, 0.2g. of platinum oxide catalyst, and 300 ml. of ethyl acetate. Shaking for 20.5 hours under 50 psi pressure resulted in the uptake of 3.18 mole equivalents (98.6%) of hydrogen. The catalyst was removed by filtration and the solvent evaporated from the filtrate. The resulting solid was dissolved in 200 ml. of ethanol and 14.62g. (0.12 mole) of ethyl methylcarboximidate hydrochloride added. After 48 hours at room temperature, the solvent was removed and the residue dissolved in chloroform and filtered.

Removal of the chloroform by distillation followed by recrystallization of the residue from hexane gave 20.3g. (71.9%) of the product as yellow-red crystals, m.p. 118°–119°C.

EXAMPLE III

6-Chloro-1-ethyl-2-methyl-7-nitro-5-trifluoromethylbenzimidazole

To a solution of 11.0g. (0.04 mole) of 6-chloro-1-ethyl-2-methyl-5-trifluoromethylbenzimidazole dissolved in 110 ml. of concentrated sulfuric acid was added 11 ml. of 90% fuming nitric acid while cooling with an ice bath. The addition required 3 hours and the resulting red-brown solution was stirred for 6 hours at 0°C. and then at room temperature for 2.5 days. After pouring onto ice, the product was precipitated by the addition of 350 ml. of concentrated ammonium hydroxide. The crude solid was isolated and dissolved in 300 ml. of chloroform. The chloroform solution was washed with water, dried over $Na_2SO_4$, filtered, and the filtrate evaporated. Crystallization of the residual solid from hexane —$CCl_4$ (3:1) gave 9.0g. (70%) of reddish solid, m.p. 114°–116°C., whose nuclear magnetic resonance pattern confirmed it to be the desired product.

EXAMPLE IV

7-Amino-6-chloro-1-ethyl-2-methyl-5-trifluoromethylbenzimidazole

About 5g. (0.0166 mole) of 6-chloro-1-ethyl-2-methyl-7-nitro-5-trifluoromethylbenzimidazole was hydrogenated in 100 ml. of methanol in the presence of 0.15g. of platinum oxide. The theoretical amount of hydrogen was absorbed in 4 hours of shaking. After filtration and removal of the methanol, the crude product was crystallized from carbon tetrachloride to give 2.3g. (51%) of reddish-brown solid, m.p. 176°–178°C. An nmr spectrum confirmed the structure as 7-amino-6-chloro-1-ethyl-2-methyl-5-trifluoromethylbenzimidazole.

EXAMPLE V

N-Ethyl-3-methoxy-6-nitro-4-trifluoromethylaniline

A solution of 14.0g. (0.052 mole) of N-ethyl-3-chloro-6-nitro-4-trifluoromethylaniline and 16.98g. (0.057 mole) of 18.23% methanolic sodium methoxide in 25 ml. of anhydrous methanol was sealed in a glass tube and heated at 119°C. for 88 hours. Removal of the solvent by distillation left a yellow solid residue which was triturated with hot chloroform. Filtration and evaporation of chloroform from the filtrate gave a crude solid residue. Crystallization of the residue from ethanol gave 12.4g. of yellow crystalline product, m.p. 140.5°–141.5°C. shown by its nmr spectrum to be the desired methoxyaniline.

EXAMPLE VI

1-Ethyl-6-methoxy-2-methyl-5-trifluoromethylbenzimidazole

A solution of 24.4g. (0.09 mole) of N-ethyl-3-methoxy-6-nitro-4-trifluoromethylaniline in 200 ml. of ethyl acetate, plus 100 ml. of ethanol, was hydrogenated in the presence of 0.2g. of platinum oxide at room temperature. The theoretical amount of hydrogen was absorbed in 19 hours of shaking at 60 psi. The catalyst was removed by filtration and the solvent evaporated at reduced pressure. The solid residue was dissolved in 200 ml. of absolute ethanol and 12.58g. (0.10 mole) of ethyl methylcarboximidate hydrochloride added. The mixture was stirred overnight at room temperature and the solvent removed at reduced pressure. Trituration of the brown residue with 200 ml. of chloroform, filtration, and evaporation of solvent from the filtrate left the crude residual product. Crystallization from hexane—$CCl_4$ (3:1) gave 18.1g. (76%) of brown, shiny needles. Recrystallization from hexane gave the pure product, m.p. 127°–129.5°C. whose structure was confirmed by an nmr spectrum.

EXAMPLE VII

1-Ethyl-6-methoxy-2-methyl-7-nitro-5-trifluoromethylbenzimidazole

1-Ethyl-6-methoxy-2-methyl-5-trifluoromethylbenzimidazole (11.0g.; 0.04 mole) was added in portions over 3 hours to a cooled mixture of 110 ml. of concentrated sulfuric acid and 11 ml. of 90% white fuming nitric acid. The resulting brown solution was held at 0°C. for 6 hours and then at 25°C. for 3 days. Addition to ice water followed by neutralization with 350 ml. of concentrated aqueous ammonia gave a brown, oily precipitate. The product was extracted thrice with 100 ml. of chloroform, the extracts washed with water, dried over $Na_2SO_4$, filtered, and the chloroform removed by distillation. The residue was crystallized from 3:1 hexane—$CCl_4$ to give 5.5g. (42.7%) of yellow solid. Recrystallization from hexane gave the desired product, m.p. 84°–85.5°C.

EXAMPLE VIII

7-Amino-1-ethyl-6-methoxy-2-methyl-5-trifluoromethylbenzimidazole

1-Ethyl-6-methoxy-2-methyl-7-nitro5-trifluoromethylbenzimidazole (3.88g.; 0.01 mole) in 50 ml. of ethyl acetate was hydrogenated in the presence of 0.1g. of platinum oxide catalyst. Shaking for 20.5 hours at room temperature resulted in the uptake of 80% of the amount of hydrogen needed to reduce the nitro group. Filtration to remove the catalyst was followed by solvent removal and trituration with hot $CCl_4$. The hot $CCl_4$ solution was filtered and the solvent evaporated at reduced pressure leaving 3.3g. (95%) of solid product. Two recrystallizations from $CCl_4$ gave the pure product, m.p. 171.5°–174.5°C.

EXAMPLE IX

7-Amino-1-ethyl-2-methyl-5-trifluoromethylbenzimidazole

N-Ethyl-2,6-dinitro-4-trifluoromethylaniline was hydrogenated in 200 ml. of ethyl acetate in the presence of 0.15g. of platinum oxide catalyst. One hour of shaking was sufficient for the absorption of enough hydrogen to reduce both nitro groups. The catalyst was removed by filtration and the ethyl acetate evaporated leaving an orange viscous residue. The latter was dissolved in 100 ml. of ethanol and 4.87g. (0.04 mole) of ethyl methylcarboximidate hydrochloride added. This mixture was stirred at room temperature for 16 hours, the solvent removed, and the residue triturated with 250 ml. of chloroform. Filtration and removal of the chloroform left a crude solid that was crystallized from $CCl_4$ to give 6.66g. (76.5%) of product, m.p. 143.5°–145°C. An nmr spectrum was consistent with the structure of 7-amino-1-ethyl-2-methyl-5-trifluoromethylbenzimidazole. After recrystallization from CCl₄, the product melts at 131°–132°C.

EXAMPLE X

7-Amino-6-bromo-1-ethyl-2-methyl-5-trifluoromethyl(benzimidazole

7-Amino-1-ethyl-2-methyl-5-trifluoromethylbenzimidazole (0.8g.; 3.3 moles) was dissolved in 15 ml. of acetic acid. To this solution, bromine (0.525g.; 3.3 moles) dissolved in 10 ml. of acetic acid, was added drop-wise with stirring and cooling. The solution was stirred for one hour after the addition was completed, and then poured into ice-water. The mixture was neutralized with aqueous sodium hydroxide and extracted twice with 100 ml. of chloroform. The chloroform was evaporated to dryness and the residue found to be a mixture of 7-amino-6-bromo-1-ethyl-2-methyl-5-trifluoromethylbenzimidazole and the corresponding 4-bromo isomer. The more soluble 6-bromo isomer was separated by digestion in 30 ml. of chloroform. The crystalline 6-bromo isomer was obtained in 36% yield; m.p. 171°–174°C.

EXAMPLE XI

6-Chloro-1-ethyl-2-methyl-7-methylamino-5-trifluoromethylbenzimidazole

To 1.0g. of 7-amino-6-chloro-1-ethyl-2-methyl-5-trifluoromethylbenzimidazole (Example IV) dissolved in 10 ml. of concentrated H₂SO₄ was added 1.0g. of paraformaldehyde. The resultant mixture was stirred at 80°C. for 2 hours and then poured onto ice. The resultant brown solution was made basic by addition of concentrated NH₄OH, precipitating a light brown solid. The mixture was extracted with chloroform and the chloroform extracts washed with water and dried over Na₂SO₄. After removal of the chloroform by evaporation, the residue was extracted with hexane and the hexane extract distilled to dryness. The solid residue was recrystallized from hexane to give 0.77g. (73.3%) of the desired product, m.p. 116.5°–119°C.

EXAMPLE XII

7-Amino-6-chloro-1-ethyl-5-trifluoromethylbenzimidazole

6-Chloro-1-ethyl-7-nitro-5-trifluoromethylbenzimidazole (3.54g.; 0.012 mole; m.p. 126.5°–128°C.) was hydrogenated in the presence of platinum oxide catalyst in accordance with the procedure of Example IV. The product was obtained as a white crystalline solid (1.54g.; 48.9%) which, after recrystallization from a CCl₄—CHCl₃ mixture, melts at 191.5°–193°C.

EXAMPLE XIII

6-Dimethylamino-1-ethyl-2-methyl-7-nitro-5-trifluoromethylbenzimidazole

A glass reaction tube was charged with 5.0g. (0.016 mole) of 6-chloro-1-ethyl-2-methyl-7-nitro-5-trifluoromethylbenzimidazole, 20 ml. of dimethoxyethane and 15 ml. of dimethylamine and then sealed. The sealed tube was maintained at 125°C. for 16 days and then opened. The contents were evaporated to dryness and the residue extracted with hot hexane, from which crystallized 3.1g. of the desired product m.p. 111°–115°C. after recrystallization from hexane.

EXAMPLE XIV

7-Amino-6-dimethylamino-1-ethyl-2-methyl-5-trifluoromethylbenzimidazole

6-Dimethylamino-1-ethyl-2-methyl-7-nitro-5-trifluoromethylbenzimidazole (1.5g.) was hydrogenated in the presence of platinum oxide catalyst according to the procedure of Example IV to give 0.83g. of the desired product, m.p. 141°–142.5°C.

EXAMPLE XV

7-Amino-2,6-dichloro-1-ethyl-5-trifluoromethylbenzimidazole

6-Chloro-1-ethyl-5-trifluoromethylbenzimidazolone was prepared by reaction of N¹-ethyl-4-trifluoroethyl-5-chloro-1,2-phenylenediamine with phosgene. The resultant benzimidazolone was chlorinated with POCl₃—HCl to give the corresponding 2-chlorobenzimidazole which was then nitrated with HNO₃—H₂SO₄ to give the 7-nitro derivative. The 2,6-dichloro-1-ethyl-7-nitro-5-trifluoromethylbenzimidazole (5g.) was hydrogenated in the presence of platinum oxide catalyst according to the procedure of Example IV to give 1.91g. (42.2%) of the desired product, m.p. 134°–141.5°C.

EXAMPLE XVI

7-Amino-6-chloro-1-(dimethylamino)-2-methyl-5-trifluoromethylbenzimidazole

A solution of 5.2g. of N²-(dimethylamino)-4-chloro-3-nitro-5-trifluoromethyl-1,2-phenylenediamine (prepared by hydrogenation of the corresponding 3,5-dinitro-4-hydrazinobenzotrifluoride in the presence of palladium catalyst) and 7.5g. of ethyl methylcarboximidate hydrochloride in 60 ml. of ethanol was refluxed for 26 hours. The resultant 7-nitrobenzimidazole was separated by fractionation on a silica gel column and then hydrogenated in the presence of platinum oxide catalyst in dimethoxyethane-methanol to give the desired product (2.8g.) m.p. 173°–174°C.

EXAMPLE XVII

7-Amino-6-chloro-1-(2-hydroxyethyl)-5-trifluoromethylbenzimidazole

A mixture of 0.5g. of 4-chloro-N²-(β-hydroxyethyl)-3-nitro-5-trifluoromethyl-1,2-phenylenediamine and 0.5g. of formic acid was refluxed in 40 ml. of 4N hydrochloric acid for 24 hours. The resultant mixture was neutralized with ammonium hydroxide, extracted with chloroform, dried and then evaporated to dryness. The resultant nitro-benzimidazole melts at 147°–150°C. after recrystallization from chloroform. It was hydrogenated in the presence of PtO₂ to give the desired 7-aminobenzimidazole, m.p. 235°–236°C.

EXAMPLE XVIII

7-Amino-6-chloro-2-(dimethylamino)-1-ethyl-5-trifluoromethylbenzimidazole

To a solution of 2.86g. of 4-chloro-N²-ethyl-3-nitro-5-trifluoromethyl-1,2-phenylenediamine in 120 ml. of chloroform was added, slowly, 2.50g. of N,N-dimethylphosgeneimmonium chloride with stirring. After the addition was completed, the resultant mixture was refluxed for 3 days and then poured into an ice-water mixture. After neutralization with sodium hydroxide, the organic phase was separated, dried and evaporated to dryness. The solid residue was washed with n-hexane-ether mixture to leave 1.0g. of yellow crystalline nitrobenzimidazole, m.p. 121°–122°C. The 7-nitrobenzimidazole was hydrogenated in the presence of PtO$_2$ catalyst to give the corresponding 7-aminobenzimidazole (1.1g.) m.p. 99°–100°C.

Other compounds representative of the present invention, which can be prepared according to the above-described procedures, include:

7-Amino-6-chloro-1-N-propyl-5-trifluoromethylbenzimidazole, m.p. 108°–111.5°C.

7-Amino-6-chloro-1-isopropyl-5-trifluoromethylbenzimidazole, m.p. 136.5°–137.5°C.

7-Amino-6-chloro-2-isopropyl-5-trifluoromethylbenzimidazole, m.p. 159.5°–160.5°C.

7-Amino-1-sec-butyl-6-chloro-5-trifluoromethylbenzimidazole, m.p. 121.5°–122.5°C.

6,7-Diamino-1-ethyl-2-methyl-5-trifluoromethylbenzimidazole, m.p. 189.5°–192°C.

7-Methylamino-1-ethyl-2-methyl-6-methoxy-5-trifluoromethylbenzimidazole, m.p. 109°–110.5°C.

7-Amino-6-chloro-1-cyclopropyl-2-methyl-5-trifluoromethylbenzimidazole, m.p. 197°–201°C.

7-Amino-6-chloro-1-isopropyl-2-n-propyl-5-trifluoromethylbenzimidazole, m.p. 106°–114°C.

7-Amino-6-chloro-1,2-diisopropyl-5-trifluoromethylbenzimidazole, m.p. 145°–149°C.

7-Amino-6-chloro-1-isopropyl-2-methyl-5-trifluoromethylbenzimidazole, m.p. 158.5°–159.5°C.

7-Amino-6-chloro-2-ethyl-1-isopropyl-5-trifluoromethylbenzimidazole, m.p. 125°–127°C.

7-Amino-6-chloro-2-ethyl-1-n-propyl-5-trifluoromethylbenzimidazole, m.p. 128.5°–130°C.

7-Amino-6-chloro-2-ethyl-5-trifluoromethylbenzimidazole, m.p. 110.5°–118.5°C.

7-Amino-6-chloro-2-isopropyl-1-methyl-5-trifluoromethylbenzimidazole, m.p. 166°–168°C.

7-Amino-6-chloro-2-methyl-5-trifluoromethylbenzimidazole, m.p. 135.5°–142.5°C.

7-Amino-6-chloro-1,2-diethyl-5-trifluoromethylbenzimidazole, m.p. 163°–164°C.

7-Amino-6-chloro-1-ethyl-2-isopropyl-5-trifluoromethylbenzimidazole, m.p. 150.5°–154.5°C.

7-Amino-6-chloro-1,2-dimethyl-5-trifluoromethylbenzimidazole, m.p. 223°–228°C.

7-Amino-1-n-butyl-2-methyl-6-chloro-5-trifluoromethylbenzimidazole, m.p. 149°–150.5°C.

7-Amino-1-isobutyl-2-methyl-6-chloro-5-trifluoromethylbenzimidazole, m.p. 178°–179°C.

7-Amino-1-sec-butyl-2-methyl-6-chloro-5-trifluoromethylbenzimidazole, m.p. 142°–143°C.

7-Amino-1-(3-pentyl)-2-methyl-6-chloro-5-trifluoromethylbenzimidazole, m.p. 161.5°–162°C.

7-Amino-2-methyl-5-trifluoromethylbenzimidazole, m.p. 190.5°–191.5°C.

7-Amino-2-isopropyl-5-trifluoromethylbenzimidazole, m.p. 179°–180°C.

7-Amino-6-chloro-1-ethyl-2-hydroxymethyl-5-trifluoromethylbenzimidazole, m.p. 182°–184°C.

7-Amino-6-chloro-2-(dimethylamino)-1-isopropyl-5-trifluoromethylbenzimidazole, m.p. 90°–91°C.

7-Amino-2-methyl-1-isopropyl-5-trifluoromethylbenzimidazole, m.p. 102°C.

7-Amino-6-chloro-1-(2-methoxy-1-methylethyl)-2-methyl-5-trifluoromethylbenzimidazole, m.p 121°–123°C.

7-Amino-1,2-dimethyl-6-methoxy-5-trifluoromethylbenzimidazole, m.p. 169°–170°C.

7-Amino-1-isopropyl-6-methoxy-2-methyl-5-trifluoromethylbenzimidazole, m.p. 155.5°–157°C.

7-Amino-2-chloro-1-ethyl-6-methoxy-5-trifluoromethylbenzimidazole, m.p. 158.5°–161°C.

7-Amino-1-(2-bromoethyl)-6-chloro-2-methyl-5-trifluoromethylbenzimidazole, m.p. 149.5°–152°C.

7-Amino-2,6-dichloro-1-isopropyl-5-trifluoromethylbenzimidazole, m.p. 156°–162°C.

The compounds of this invention are excellent herbicides and can be applied as both a pre-emergence or a post-emergence treatment; that is, they can be applied to soil in which the weeds will grow or, they can be used to kill or suppress the growth of weeds or to kill or prevent the emergence of seedlings of undesirable plants. Thus, the benzimidazoles can be used to control the growth of weeds by applying a phytotoxic amount of one or more of the active compounds of this invention to the locus to be protected; that is, soil in which the weeds are growing or will grow, or the foliage of the growing plants. When used as a pre-emergence treatment, the compounds may be incorporated, such as by mixing into the top 1–3 inches of soil prior to planting the crop, if desired. "Weeds" as used herein is meant to include any plant growth which is undesirable.

The compounds are especially useful as post-emergence herbicides for selectively controlling weeds in the presence of desirable crops, such as corn, wheat, barley, rice and sorghum. Hard-to-control weeds such as foxtail, valvet-leaf, pigweed, Jimsonweed, teaweed, morning-glory and cocklebur are killed at relatively low rates of application with little or no injury to the crop.

Generally, an application rate of from about 0.2 to about 15 pounds of one or more of the active compounds per acre is effective in controlling plant growth. Preferably, an application rate in the range of from about 0.5 to about 5 pounds per acre is employed. At such rates, the undesirable weeds are killed or stunted with little or no injury to desirable crops.

The following examples illustrate the herbicidal activity of typical compounds of this invention.

EXAMPLE XIX

The compounds to be tested were evaluated as both a preemergence and post-emergence treatment. Greenhouse flats were planted to soybeans (SB), velvetleaf (VL), oats (O) and millet (M) and the flats sprayed on the same day as planting with an ethanol solution of the compound to be tested at a rate of 5 pounds per acre.

Another set of flats with the same plants was treated after the plants had emerged and were about 1 inch in height. These flats were also sprayed with an ethanol solution of the compound to be tested at a rate of 5 pounds per acre. The flats were kept in the greenhouse and watered when needed. Twenty-one days after treatment, the flats were examined and the plants rated for herbicidal activity on a 0 to 9 scale in which 0 = no effect, 5 = substantial injury with some kill, and 9 = complete kill. The results are shown in Table I.

TABLE I

| Compound | Activity PRE | | | | | POST | | |
|---|---|---|---|---|---|---|---|---|
| | SB | VL | O | M | SB | VL | O | M |
| 7-amino-6-chloro-1-isopropyl-5-trifluoromethyl-benzimidazole | 0 | 5 | 0 | 2 | 5 | 9 | 5 | 9 |
| 7-amino-6-chloro-1-isopropyl-2-methyl-5-trifluoromethylbenzimidazole | 2 | 8 | 5 | 7 | 9 | 9 | 8 | 9 |
| 7-amino-6-chloro-2-ethyl-1-isopropyl-5-trifluoromethylbenzimidazole | 1 | 1 | 1 | 1 | 9 | 9 | 8 | 9 |
| 7-amino-6-chloro-1-isopropyl-2-n-propyl-5-trifluoromethylbenzimidazole | 2 | 1 | 0 | 0 | 2 | 2 | 1 | 2 |
| 7-amino-6-chloro-2-isopropyl-1-n-propyl-5-trifluoromethylbenzimidazole | 0 | 0 | 0 | 0 | 2 | 1 | 1 | 1 |
| 7-amino-6-chloro-2-methyl-1-n-propyl-5-trifluoromethylbenzimidazole | 1 | 1 | 0 | 1 | 1 | 5 | 1 | 1 |
| 7-amino-6-chloro-2-ethyl-5-trifluoromethyl-benzimidazole | 0 | 0 | 0 | 0 | 0 | 8 | 0 | 5 |
| 7-amino-6-chloro-2-isopropyl-1-methyl-5-trifluoromethylbenzimidazole | 0 | 1 | 1 | 2 | 5 | 9 | 1 | 8 |
| 7-amino-6-chloro-2-methyl-5-trifluoromethyl-benzimidazole | 0 | 0 | 0 | 2 | 1 | 8 | 1 | 7 |
| 7-amino-6-chloro-1,2-diethyl-5-trifluoromethylbenzimidazole | 0 | 6 | 5 | 5 | 7 | 7 | 5 | 9 |
| 7-amino-1-sec butyl-6-chloro-5-trifluoromethylbenzimidazole | 0 | 0 | 0 | 0 | 0 | 0 | 0 | 7 |
| 6,7-diamino-1-ethyl-2-methyl-5-trifluoromethylbenzimidazole | 0 | 0 | 0 | 0 | 1 | 8 | 0 | 5 |
| 7-amino-1-ethyl-2-methyl-6-methoxy-5-trifluoromethylbenzimidazole | 9 | 9 | 9 | 9 | 9 | 8 | 9 | 9 |
| 7-methylamino-1-ethyl-2-methyl-6-chloro-5-trifluoromethylbenzimidazole | 5 | 0 | 1 | 8 | 9 | 8 | 5 | 9 |
| 7-methylamino-1-ethyl-2-methyl-6-methoxy-5-trifluoromethylbenzimidazole | 9 | 6 | 6 | 9 | 9 | 9 | 8 | 9 |
| 7-amino-1-ethyl-2-methyl-6-dimethylamino-5-trifluoromethylbenzimidazole | 8 | 8 | 6 | 8 | 7 | 9 | 8 | 9 |
| 7-methylamino-1-ethyl-2-methyl-5-trifluoromethylbenzimidazole | 2 | 9 | 6 | 9 | 5 | 9 | 6 | 9 |
| 7-amino-4-chloro-1-ethyl-6-methoxy-2-methyl-5-trifluoromethylbenzimidazole | 0 | 0 | 0 | 0 | 5 | 6 | 6 | 7 |
| 7-amino-4,6-dichloro-1-ethyl-2-methyl-5-trifluoromethylbenzimidazole | 1 | 1 | 1 | 1 | 7 | 8 | 2 | 7 |
| 7-amino-6-chloro-1,2-dimethyl-5-trifluoromethylbenzimidazole | 1 | 8 | 6 | 9 | 8 | 7 | 8 | 9 |
| 7-amino-6-chloro-1-(1-methyl-2-methoxyethyl)-2-methyl-5-trifluoromethylbenzimidazole | 3 | 8 | 2 | 1 | 9 | 9 | 7 | 8 |
| 7-amino-6-chloro-1-(2-bromoethyl)-2-methyl-5-trifluoromethylbenzimidazole | 0 | 0 | 0 | 0 | 6 | 9 | 1 | 8 |
| 7-amino-6-chloro-1-(2-hydroxyethyl)-5-trifluoromethylbenzimidazole | 5 | 5 | 7 | 7 | 9 | 9 | 1 | 8 |
| 7-amino-2,6-dichloro-1-isopropyl-5-trifluoromethylbenzimidazole | 2 | 2 | 0 | 0 | 6 | 9 | 7 | 9 |
| 7-amino-1,2-dimethyl-6-methoxy-5-trifluoromethylbenzimidazole | 8 | 7 | 7 | 7 | 9 | 8 | 8 | 8 |
| 7-amino-1-isopropyl-6-methoxy-2-methyl-5-trifluoromethylbenzimidazole | 9 | 9 | 9 | 9 | 9 | 9 | 8 | 9 |
| 7-amino-2-chloro-1-ethyl-6-methoxy-5-trifluoromethylbenzimidazole | 2 | 8 | 7 | 8 | 8 | 8 | 7 | 9 |
| 7-amino-6-chloro-1-ethyl-2-(hydroxymethyl)-5-trifluoromethylbenzimidazole | 0 | 7 | 0 | 0 | 0 | 9 | 0 | 0 |
| 7-amino-6-chloro-2-(dimethylamino)-1-ethyl-5-trifluoromethylbenzimidazole | 0 | 0 | 0 | 0 | 0 | 8 | 5 | 9 |
| 7-amino-6-chloro-1-isopropyl-2-(dimethylamino)-5-trifluoromethylbenzimidazole | 0 | 0 | 0 | 0 | 1 | 5 | 2 | 7 |

EXAMPLE XX

7-Amino-1-ethyl-2-methyl-6-chloro-5-trifluoromethylbenzimidazole was evaluated as a post-emergence treatment on a broad class of representative crops and weeds. The compound and its hydrochloride salt were tested according to the procedure of Example XIX at a rate of one pound per acre. The hydrochloride salt was dissolved in water. The results are shown in Table II.

TABLE II

| Plant | Compound | HCl Salt |
|---|---|---|
| Cotton | 5/3 | 9 |
| Corn | 0 | 1 |
| Soybeans | 7/2 | 9 |
| Wheat | 1 | 0 |
| Barley | 1 | 1 |
| Field Beans | 9 | 7/3 |
| Mustard | 9 | 8/4 |
| Foxtail | 9 | 8/3 |
| Coffeeweed | 9 | — |
| Velvetleaf | 9 | 9 |
| Millet | 9 | 9 |
| Peanuts | 5/3 | 2 |
| Pigweed | 9 | 9 |
| Jimsonweed | 7/3 | 8/4 |
| Teaweed (Prickly sida) | 6/4 | 8/4 |
| Watergrass | 8/4 | 7/3 |
| Morning-glory | 9 | 9 |
| Sorghum | 5/3 | 1 |
| Rice | — | 1 |

In Table II, where there are two numbers, i.e. 7/3, first is percent kill on a 5–9 scale and the second percent injury to remaining plants on a 0–4 scale. Tl 0 = no effect
1 = <10% injury
2 = 10-40% injury
3 = 40-70% injury
4 => 70% injury
5 = <25% kill
6 = 25-50% kill
7 = 50-75% kill
8 = 75-99% kill
9 = complete kill

EXAMPLE XXI

Three compounds of the present invention and a known position isomer were tested as post-emergence herbicides at a rate of 1 pound per acre on a group of representative crops and weeds. The procedure of Example XX was followed. The results were as shown in Table III.

The examples in Table III show the unexpected superiority of the compounds of the present invention having 7-amino and 5-trfluoromethyl substituents when compared with the known 6-amino isomer. See British Pat. No. 1,111,905 (French Pat. No. 1,482,315; *Chemical Abstracts* 68, 101597b [1968]). The 7-amino-substituted compounds are especially useful against the hard-to-control weeds cocklebur, velvetleaf, teaweed, morning-glory, jimsonweed and pigweed.

EXAMPLE XXII

Additional compounds were tested as a post-emergence herbicide at a rate of 1 or 0.75 pound per acre on a group of representative crops and weeds according to the procedure of Examples XX and XXI. The results were as set forth in Table IV.

TABLE IV

| Plant | Cmpd. E | Cmpd. F | Activity Cmpd. G | Cmpd. H* | Cmpd. J* |
|---|---|---|---|---|---|
| Alfalfa | 0 | 0 | 6/1 | — | — |
| Cotton | 3 | 1 | 6/2 | 9 | 9 |
| Soybeans | 1 | 1 | — | 9 | 3 |
| Peanuts | 0 | 0 | 0 | 3 | 2 |
| Corn | 1 | 0 | 0 | 1 | 1 |
| Wheat | 1 | 2 | 0 | 2 | 1 |
| Rice | 0 | 0 | 2 | 3 | 2 |
| Field beans | 2 | 0 | 5/2 | — | — |
| Velvetleaf | 9 | 8/2 | 8/2 | 9 | 9 |
| Pigweed | 9 | 8/4 | 9 | 9 | 9 |
| Jimsonweed | 9 | — | — | 8/2 | 6/1 |
| Teaweed | 8/3 | 6/2 | 9 | 9 | 9 |
| Morning-glory | 2 | 7/2 | 8/2 | 9 | 9 |
| Foxtail | 5/2 | 5/2 | 7/3 | 9 | 8/1 |
| Watergrass | 7/3 | 6/1 | 8/2 | 9 | 8/2 |
| Mustard | 9 | 9 | 9 | 9 | 9 |
| Ragweed | 5/2 | 6/2 | 6/2 | 9 | 9 |
| Wildoats | 2 | 6/2 | 8/3 | 6/3 | 7/3 |
| Sicklepod | — | — | — | 9 | 8/4 |
| Purslane | — | — | — | 9 | 9 |
| Sesbania | — | — | — | 8/2 | 9 |
| Ironweed | — | — | — | 9 | 9 |
| Lambsquarters | — | — | — | 9 | 9 |
| Groundcherry | — | — | — | 9 | 9 |
| Cocklebur | — | — | — | 9 | 9 |
| Crabgrass | — | — | — | 9 | 9 |
| Sandbur | — | — | — | 7/1 | 7/2 |
| Johnsongrass | — | — | — | 8/4 | 5/3 |

Compound E = 7-amino-6-chloro-1-dimethylamino-2-methyl-5-trifluoromethylbenzimidazole
Compound F = 7-amino-6-chloro-1-(2-methoxy-1-methylethyl)-2-methyl-5-trifluoromethylbenzimidazole
Compound G = 7-amino-2,6-dichloro-1-ethyl-5-trifluoromethylbenzimidazole
Compound H = 7-amino-6-chloro-1-isopropyl-2-methyl-5-trifluormethylbenzimidazole
Compound J = 7-amino-2-methyl-1-isopropyl-5-trifluoromethylbenzimidazole
*applied at 0.75 pound per acre

TABLE III

| Plant | Cmpd. A | Cmpd. B | Activity Cmpd. C | Cmpd. D |
|---|---|---|---|---|
| Corn | 1 | 0 | 0 | 1 |
| Sorghum | 5/3 | 5/2 | 5/1 | 5/2 |
| Wheat | 2 | 5/2 | 6/2 | 5/2 |
| Barley | 1 | 5/2 | 5/2 | 5/2 |
| Velvetleaf | 6/2 | 8/3 | 7/3 | 1 |
| Cotton | 0 | 9 | 9 | 5/2 |
| Morning-glory | 9 | 9 | 9 | 1 |
| Jimsonweed | 5/2 | 8/3 | 9 | 5/3 |
| Rice | 1 | 2 | 2 | 0 |
| Teaweed | 2 | 8/4 | 9 | 5/1 |
| Pigweed | 7/3 | 9 | 9 | 1 |
| Foxtail | 8/4 | 7/3 | 6/3 | 0 |
| Proso-millet | — | 8/4 | 9 | 5/1 |
| Watergrass | — | 8/4 | 8/3 | 0 |
| Crabgrass | — | 9 | 8/3 | 0 |
| Mustard | — | 9 | 8/3 | 0 |
| Johnsongrass | — | 2 | 1 | 1 |
| Cocklebur | — | 9 | 9 | 1 |

Compound A = 7-amino-1-ethyl-2-isopropyl-6-chloro-5-trifluoromethylbenzimidazole
Compound B = 7-amino-1-ethyl-2-methyl-6-bromo-5-trifluoromethylbenzimidazole
Compound C = 7-amino-1-ethyl-2-methyl-5-trifluoromethylbenzimidazole
Compound D = 6-amino-1-ethyl-2-methyl-5-trifluoromethylbenzimidazole Since a relatively small amount of one or more of the active benzimidazoles should be uniformly distributed over the area to be treated, the compounds preferably are formulated with conventional herbicide carriers, either liquid or solid. Thus, the compounds can be impregnated on or admixed with a pulverulent solid carrier such as lime, talc, clay, Bentonite, calcium chloride, vermiculite, and the like. Alternatively, the compounds can be dissolved or suspended in a liquid carrier such as water, kerosene, alcohols, diesel oil, xylene, benzene, glycols, ketones, and the like. Since many of the compounds will form water-soluble salts such as with mineral acids, they can be formulated with water.

A surfactant is preferably included to aid in dispersion, emulsification and coverage. The surfactant can be ionic or nonionic, and may be liquid or a solid. The use of the term "surfactant" herein is intended to include such compounds commonly referred to as wetting agents, dispersing agents and emulsifying agents. Typical surfactants include the alkylarylsulfonates, the fatty alcohol sulfates, sodium salt of napthalenesulfonic acid, alkylaryl polyether alcohols, long chain quaternary ammonium compounds, sodium salts of petroleum-derived alkylsulfonic acids, polyoxyethylene-sorbitan monolaurate, and the like. These dispersing and wetting agents are sold under numerous trademarks and may either be pure compounds, mixtures of compounds of the same general group, or they can be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with a locally available carrier, preferably water, thereby keeping shipping costs to a minimum while providing a product which can be used with a minimum of equipment and effort. Such concentrates may contain from about 5 to about 95 percent by weight of one or more of the active benzimidazoles with a carrier or diluent, which may be a liquid or solid. Liquid carriers which are miscible with the active agent or other liquids in which the compound may be suspended or dispersed, can be used. A surfactant is also generally included to facilitate such dilution or dispersion in water. However, the surfactant itself may comprise the carrier in such concentrates.

The herbicidal compositions can include other beneficial adjuvants, such as humectants, oils and contact agents. Further, other herbicides such as the chlorophenoxyacetic acids, substituted uracils and ureas, triazines, dinitroanilines, carbamates, 1,3-phenylenediamines, anilides, amides, and halo-alkanoic acids, can be included in the formulation, if desired.

Various changes and modifications of the invention can be made, and, to the extent that such variations incorporate the spirit of this invention, they are intended to be included within the scope of the appended claims.

What is claimed is:

1. A herbicidal composition comprising an herbicidally effective amount of a compound of the formula

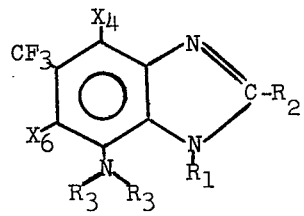

in which $R_1$ represents hydrogen, lower alkyl, halo-substituted lower alkyl, lower cycloalkyl, halo-substituted lower cycloalkyl, hydroxy-substituted lower alkyl, lower alkoxy-substituted lower alkyl or di-lower alkylamino, $R_2$ represents hydrogen, lower alkyl, lower cycloalkyl, hydroxy-substituted lower alkyl, lower alkoxy-substituted lower alkyl, halo, or di-lower alkylamino, each $R_3$ is selected from the group consisting of hydrogen and lower alkyl, and each of $X_4$ and $X_6$ represents hydrogen, halo, lower alkoxy or amino of the formula

and in which not more than one of said $R_1$ and $R_2$ represents hydrogen and not more than one of said $X_4$ and $X_6$ represents

and a carrier therefore.

2. A herbicidal composition according to claim 1 in which a surfactant is included.

3. The method for controlling unwanted plant growth which comprises applying to the locus of said plant growth, a phytotoxic amount of a compound of the formula

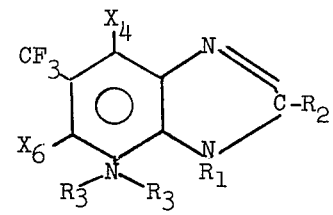

in which $R_1$ represents hydrogen, lower alkyl, halo-substituted lower alkyl, lower cycloalkyl, halo-substituted lower cycloalkyl, hydroxy-substituted lower alkyl, lower alkoxy-substituted lower alkyl or di-lower alkylamino, $R_2$ represents hydrogen, lower alkyl, lower cycloalkyl, hydroxy-substituted lower alkyl, lower alkoxy-substituted lower alkyl, halo, or di-lower alkylamino, each $R_3$ is selected from the group consisting of hydrogen and lower alkyl, and each of $X_4$ and $X_6$ represents hydrogen, halo, lower alkoxy or amino of the formula

in which not more than one of said $R_1$ and $R_2$ represents hydrogen and not more than one of said $X_4$ and $X_6$ represents

4. The method in accordance with claim 3 in which $R_1$ and $R_2$ are lower alkyl and $R_1 + R_2$ represents a total of about 2 to 6 carbon atoms.

5. The method in accordance with claim 3 in which both $R_3$'s in the 7-amino group are hydrogen.

6. The method in accordance with claim 3 in which said compound is applied at a rate of about 0.5 to 5 pounds per acre.

7. The method according to claim 3 in which said compound is applied as a post-emergence treatment.

8. The method according to claim 3 in which said compound is 7-amino-6-chloro-1-ethyl-2-methyl-5-trifluoromethylbenzimidazole.

9. The method according to claim 3 in which said compound is 7-amino-6-chloro-1-methyl-2-isopropyl-5-trifluoromethylbenzimidazole.

10. The method according to claim 3 in which said compound is 7-amino-6-methoxy-1-ethyl-2-methyl-5-trifluoromethylbenzimidazole.

11. The method according to claim 3 in which said compound is 7-amino-6-chloro-1-isopropyl-2-methyl-5-trifluoromethylbenzimidazole.

12. The method according to claim 3 in which said compound is 7-amino-1-isopropyl-2-methyl-5-trifluoromethylbenzimidazole.

13. The method according to claim 3 in which said compound is 7-amino-1-ethyl-2-methyl-5-trifluoromethylbenzimidazole.

14. The herbicidal composition in accordance with claim 1 in which said compound is in its hydrochloride salt form.

15. The method according to claim 3 in which said compound is 7-amino-2,6-dichloro-1-isopropyl-5-trifluoromethylbenzimidazole.

16. The method according to claim 3 in which said compound is 7-amino-1-isopropyl-6-methoxy-2-methyl-5-trifluoromethylbenzimidazole.

* * * * *

UNITED STATES PATENT OFFICE
CERTIFICATE OF CORRECTION

Patent No. 3,954,438                    Dated May 4, 1976

Inventor(s) DON L. HUNTER; ROBERT A. SMITH; WAYNE S. BELLES

It is certified that error appears in the above-identified patent and that said Letters Patent are hereby corrected as shown below:

In Column 1, line 24 delete "hydroxyl" and add --hydroxy--

In Column 16, TABLE IV, under the heading Cmpd. E, for Watergrass, delete "7/3" and add --7/2--

Signed and Sealed this

Thirty-first Day of August 1976

[SEAL]

Attest:

RUTH C. MASON
*Attesting Officer*

C. MARSHALL DANN
*Commissioner of Patents and Trademarks*